United States Patent [19]

Hotchkiss et al.

[11] 4,212,820
[45] Jul. 15, 1980

[54] ACRYLAMIDE OR METHACRYLAMIDE ALKOXYPROPYL QUATERNARY COMPOUNDS

[75] Inventors: Philip Hotchkiss; Robert M. Gipson; Edward C. Y. Nieh, all of Austin, Tex.

[73] Assignee: Texaco Development Corp., White Plains, N.Y.

[21] Appl. No.: 32,317

[22] Filed: Apr. 23, 1979

[51] Int. Cl.$^2$ ............................................ C07C 103/70
[52] U.S. Cl. .................................................. 260/561 N
[58] Field of Search ....................................... 260/561 N

[56] References Cited

U.S. PATENT DOCUMENTS

| | | | |
|---|---|---|---|
| 2,810,713 | 10/1957 | Melamed | 260/561 N |
| 3,170,901 | 2/1965 | Melamed et al. | 260/561 N |
| 3,878,247 | 4/1975 | Moss et al. | 260/561 N |
| 3,957,869 | 5/1976 | Nagy | 260/561 N |
| 4,031,138 | 6/1977 | Nieh et al. | 260/561 N |
| 4,134,916 | 1/1979 | Moss et al. | 260/561 N |

OTHER PUBLICATIONS

Boothe et al. J. Macromol. Sci. A 10(8), 1976 pp. 1541-1550.

*Primary Examiner*—Arthur P. Demers
*Attorney, Agent, or Firm*—Carl G. Ries; Robert A. Kulason; James L. Bailey

[57] ABSTRACT

Covers a new composition of matter comprising an acrylamide or methacrylamide monomer characterized by the following structural formula:

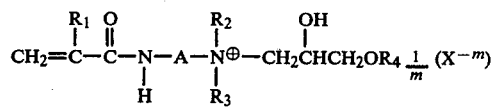

where $R_1$ is hydrogen or methyl, $R_2$ and $R_3$ are lower alkyl, $R_4$ is a linear or branched alkyl group containing 7-20 carbon atoms, X is an anion of an organic or mineral acid having a valence m and A is a divalent lower alkyl group.

4 Claims, No Drawings

ACRYLAMIDE OR METHACRYLAMIDE ALKOXYPROPYL QUATERNARY COMPOUNDS

BACKGROUND OF THE INVENTION

1. Field of the Invention

This invention relates to novel acrylamide or methacrylamide monomers.

2. Description of the Prior Act

Cationic monomers of the acrylamide or methacrylamide type are known, as typically set out in U.S. Pat. Nos. 4,031,138; 2,567,836; 2,595,907; 3,652,671; 3,661,868; 3,671,472 and 3,878,247. Specifically, quaternaries of this type are set out in U.S. Pat. Nos. 3,666,810 and 2,834,758; British Pat. No. 1,281,638 and by J. E. Boothe et al J. Macromol, Sci., A 10(8) 1541 (1976). However, there is an ever continuing effort to find novel materials of this type which may show unique utilities in areas of application not possessed by similar prior art materials of this class.

In many instances, cationic surfactants of this type are not readily polymerizable or copolymerizable. At best, monomers of this type in some cases are not sufficiently reactive in a practical sense. In addition, compounds of this type sometimes contain metal ions whose presence sometimes cannot be tolerated in certain end-use applications.

It is the object of the invention to prepare a new class of cationic acrylamides and methacrylamides which are useful in a wide variety of end-uses normally calling for ionically charged monomers of this type.

SUMMARY OF THE INVENTION

The invention relates to acrylamide or methacrylamide monomers characterized by the following formula:

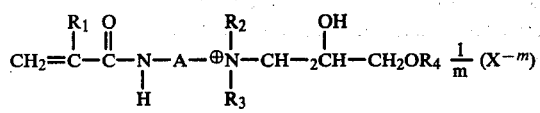

where $R_1$ is hydrogen or methyl, $R_2$ and $R_3$ are lower alkyl, $R_4$ is a linear or branched aklyl group containing 7-20 carbon atoms, X is an anion of an organic or mineral acid having a valence m and A is a divalent lower alkyl group.

DESCRIPTION OF THE PREFERRED EMBODIMENTS

The compounds of the invention described above may be prepared utilizing a number of known synthetic techniques. One typical mode of preparation involves reacting the appropriate tertiary amine substituted acrylamide or methacrylanide with a glycidyl aklyl ether and an acid, organic or mineral, preferably in an alcohol medium.

The reaction may be depicted as follows where $R_1$, $R_2$, $R_3$, $R_4$, A, m and X are as above stated.

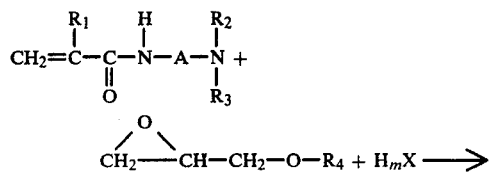

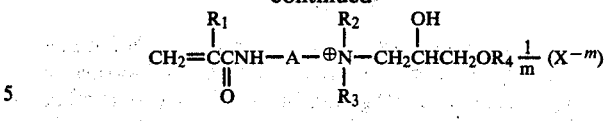

A is most preferably an ethylene or propylene group, and in any event usually contains 2-6 carbon atoms. $R_2$ and $R_3$ are most preferably methyl, ethyl or propyl (iso or n-) and usually contain 1-6 carbon atoms. $R_4$ is $C_7C_{20}$, more often $C_7$-$C_6$.

Both reactants of amine-amide and oxide are known materials and need little elaboration.

The reaction of an oxide with a basic nitrogen atom such as a tertiary amine to form a quaternary moiety is well known to those skilled in the art, and needs little explanation. This reaction may be carried out over a wide temperature range, say within 50°-200° C. The reaction is perferably conducted in a closed vessel under pressure. The particular pressure employed is not critical and autogenous pressures are generally used. Usually the acid is first added to the aminoamide followed by addition of oxide. However, acid, aminoamide, and oxide may be reacted by simultaneous addition to one another.

A wide variety of organic or inorganic acids may be employed, and thus X in the above formula defining the final products may represent anionic radicals such as halo including chloride, bromide, or iodide, mono-, di-, or tri-basic phosphate, acetate, lactate, gluconate, sulfate, nitrate, nitrite, alkylsulfate, alkyl and arylsulfonates, e.g., dipropylnapthalenesulfonate, dibutylnapthalenesulfonate, methyl-, ethyl-, propyl-, butyl-, octyl-, or dodecyl- benzenesulfonate, formate, propionate, oxalate, laurate, phenysulfonate, benzoate, borate, carbonate, etc. Preferred acids include acetic acid, hydrochloric acid, and sulfuric acid.

Usually the reaction between the aminoamide, acid and oxide is conducted in an alcoholic solution, although mixtures of water and polar materials such as methanol, ethanol, isopropanol, and the like may be employed.

The following examples illustrate preparation of typical compounds falling within the scope of the invention. It is understood that these examples are merely illustrative and that the invention is not to be limited thereto.

EXAMPLE 1

In a two liter, three neck flask equipped with mechanical stirrer, thermometer and addition funnel were charged N-3-dimethyl aminopropyl methacrylamide (170 g), 2-propanol, (500 g) and acetic acid (60 g). After the acid salt solution was heated to 50° C., linear alkyl glycidyl ether (301 g, equivalent weight 301, Proctor and Gamble Epoxide 8) was added over a period of 30 minutes. The reaction mixture was digested at 50° C. for one hour. Analysis of the resulting solution by non aqueous titration found 0.96 meq/g titratable base (acetate anion). Nmr spectra of the product mixture are consistent with that of the expected product (I)

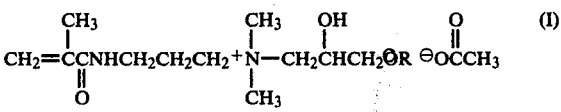

R is a linear alkyl with 8 to 14 carbon atoms

EXAMPLE 2

By a procedure similar to Example 1, N-3-dimethylaminopropyl methacrylamide (170 g) 2-propanol (469 g), acetic acid (60 g) and linear alkylglycidyl ether (239 g, equivalent weight 239, Proctor and Gamble Epoxide 7) were converted to a 50% solution of the corresponding methaerylamidopropyl-(3-alkoxy-2-hydroxypropyl) dimethylammonium acetate in 2-propanol.

EXAMPLE 3

By a procedure similar to Example 1, N-3-dimethylaminopropyl methacrylamide (170 g) methanol (500 g) acetic acid (60 g) and linear aklylglycidyl ether (301 g, equivalent weight 301, Proctor and Gamble Epoxide 7) were converted to a 50% solution of the corresponding methacrylamidopropyl-(3-alkoxy-2-hydroxylropyl) dimethylammonium acetate in methanol.

EXAMPLE 4

By a procedure similar to Example 1 N-3-dimethylaminopropyl methacrylamide (170 g), methanol (500 g), acetic acid (60 g) and linear alkyglycidyl ether (239 g, equivalent weight 239, Proctor and Gamble Epoxide 7) were converted to a 50% solution of the corresponding methacrylamidopropyl-(3-alkoxy-2-hydroxypropyl) dimethylammonium acetate in methanol.

EXAMPLE 5

The surface tension and the interfacial tension of (water/light mineral oil) solutions containing 1%, 0.1% and 0.01% of monomers prepared in Example 1 and Example 2 were measured and results are summarized below.

| Prepared in | Surface Active Monomer % | Surface Tension | Interfacial Tension |
|---|---|---|---|
| Example 1 | 1% | 29.5 | 0.3 |
| Example 1 | 0.1% | 28.5 | 0.3 |
| Example 1 | 0.01% | 34.0 | 0.4 |
| Example 2 | 1% | 27.2 | 0.3 |
| Example 2 | 0.1% | 29.0 | 0.3 |
| Example 2 | 0.01% | 45.5 | 17.4 |

In addition to the just disclosed utility of the compounds of the invention as surfactants, the cationic monomers also find use in additional areas of utility. For example, the cationic monomers, or polymers, copolymers or interpolymers, resulting therefrom may be used as coagulants, polyurethane or polyisocyanurate catalysts, retention aids for fiber furnishes in the paper industry, additives used for improving drainage through the wire surface of Fourdrinier machine, and additives in cellulosic materials for the purpose of retaining dye added thereto, as polyelectrolytes in the coagulation of low turbidity water, and as additives useful in the flocculation or dewatering of sewage, the settling of coal slurries, the coagulation of rubber latex, and the breaking of oil-in-water emulsions. Likewise, the monomers, homopolymers or interpolymers thereof may be used as additives in a number of processes or employed per se to produce a variety of manufactured articles. For example, solutions of resulting polymers may be cast or spun into shaped articles, sheets, films, wrapping tissues, tubing filaments, yarns, threads, etc. As other examples, aqueous or alcoholic solutions of polymers made from the cationic monomers described here may be used in coating, finishing casting or molding for adhesion or laminaton. Specifically, they must be used as adhesives for cellophane, paper, cloth, etc., as finishes for fabrics, as permanent sizes for yarns, as protective water resistant coverings, for use as sausage casings, as dye intermediates, as filament film formers, etc. The polymers may also find excellent use as anchoring agents for natural and synthetic filaments films and artificial leather. They may also be used to finish and impregnate or coat by surface modification or other manipulative techniques a number of industrial and commercial articles.

While the invention has been described in connection with specific embodiments thereof, it will be understood that it is capable of further modification, and this application is intended to cover any variations, uses or adaptations of the invention following, in general, the principles of the invention and including such departures as come within known or customary practice in the art to which the invention pertains and as may be applied to the essential features hereinbefore set forth, and as fall within the scope of the invention and the limits of the appended claims.

The invention is hereby claimed as follows.

1. An acrylamide or methacrylamide alkoxypropyl quaternary characterized by the following structural formula:

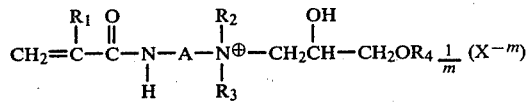

where $R_1$ is hydrogen or methyl, $R_2$ and $R_3$ are lower alkyl, $R_4$ is a linear or branched alkyl group containing 7–20 carbon atoms, X is an anion of an organic or mineral acid having a valence m and A is a divalent lower alkyl group.

2. The quaternary of claim 1 where A is propylene.

3. The quaternary of claim 2 where $R_1$ is methyl.

4. The quaternary of claim 3 where $R_2$ and $R_3$ are methyl.

* * * * *